US011092725B2

(12) United States Patent
Darty

(10) Patent No.: US 11,092,725 B2
(45) Date of Patent: Aug. 17, 2021

(54) SINGLE-SENSOR HYPERSPECTRAL IMAGING DEVICE

(71) Applicant: SAMSUNG ELECTRONICS CO., LTD., Suwon-si (KR)

(72) Inventor: Mark Anthony Darty, Collierville, TN (US)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 16/704,307

(22) Filed: Dec. 5, 2019

(65) Prior Publication Data

US 2020/0110208 A1   Apr. 9, 2020

Related U.S. Application Data

(63) Continuation of application No. 16/003,036, filed on Jun. 7, 2018, now Pat. No. 10,534,116, which is a
(Continued)

(51) Int. Cl.
*G02B 5/20* (2006.01)
*A61B 5/00* (2006.01)
(Continued)

(52) U.S. Cl.
CPC ............. *G02B 5/20* (2013.01); *A61B 5/0075* (2013.01); *G01J 3/0264* (2013.01);
(Continued)

(58) Field of Classification Search
CPC ........ G02B 5/20; A61B 5/0075; G01J 3/0264; G01J 3/2803; G01J 3/2823; G01J 3/36; H04N 5/2256; H04N 5/238; H04N 5/332
See application file for complete search history.

(56) References Cited

U.S. PATENT DOCUMENTS 5,568,186 A   10/1996   Althouse
6,831,688 B2  12/2004   Lareu et al.
(Continued)

FOREIGN PATENT DOCUMENTS

CN   201948983      8/2011
JP   2003-087806 A  3/2003
(Continued)

OTHER PUBLICATIONS

Constantinou, P. et al., "A High-Resolution MACROscope With Differential Phase Contrast, Transmitted Light, Confocal Fluorescence, and Hyperspectral Capabilities for Large-Area Tissue Imaging", IEEE Journal of Selected Topics in Quantum Electronics, the U.S., IEEE, Nov. 5, 2005, vol. 11, Issue 4, pp. 766-777.
(Continued)

*Primary Examiner* — Nicholas G Giles
(74) *Attorney, Agent, or Firm* — Sughrue Mion, PLLC

(57) ABSTRACT

The present disclosure generally relates to hyperspectral spectroscopy, and in particular, to systems, methods and devices enabling a single-sensor hyperspectral imaging device. Hyperspectral (also known as "multispectral") spectroscopy is an imaging technique that integrates multiples images of an object resolved at different narrow spectral bands (i.e., narrow ranges of wavelengths) into a single data structure, referred to as a three-dimensional hyperspectral data cube. Data provided by hyperspectral spectroscopy allow for the identification of individual components of a complex composition through the recognition of spectral signatures of individual components within the three-dimensional hyperspectral data cube.

19 Claims, 2 Drawing Sheets

Related U.S. Application Data continuation of application No. 15/681,265, filed on Aug. 18, 2017, now Pat. No. 10,018,758, which is a continuation of application No. 13/844,737, filed on Mar. 15, 2013, now Pat. No. 9,766,382.

(60) Provisional application No. 61/716,401, filed on Oct. 19, 2012, provisional application No. 61/715,273, filed on Oct. 17, 2012, provisional application No. 61/655,800, filed on Jun. 5, 2012.

(51) Int. Cl.

| | | |
|---|---|---|
| H04N 5/225 | (2006.01) | |
| H04N 5/33 | (2006.01) | |
| G01J 3/02 | (2006.01) | |
| G01J 3/28 | (2006.01) | |
| G01J 3/36 | (2006.01) | |
| H04N 5/238 | (2006.01) | |

(52) U.S. Cl.
CPC .......... *G01J 3/2803* (2013.01); *G01J 3/2823* (2013.01); *G01J 3/36* (2013.01); *H04N 5/2256* (2013.01); *H04N 5/238* (2013.01); *H04N 5/332* (2013.01); *G01J 2003/2806* (2013.01); *G01J 2003/2826* (2013.01)

(56) References Cited

U.S. PATENT DOCUMENTS

| | | | |
|---|---|---|---|
| 7,242,478 B1 * | 7/2007 | Dombrowski | G01J 3/02 356/419 |
| 7,433,042 B1 | 10/2008 | Cavanaugh et al. | |
| 7,589,772 B2 | 9/2009 | Coffman et al. | |
| 9,766,382 B2 | 9/2017 | Darty | |
| 10,018,758 B2 | 7/2018 | Darty | |
| 2006/0274308 A1 | 12/2006 | Brady et al. | |
| 2007/0206242 A1 | 9/2007 | Smith | |
| 2008/0123097 A1 | 5/2008 | Muhammed et al. | |
| 2008/0204744 A1 * | 8/2008 | Mir | H04N 5/3415 356/303 |
| 2009/0073451 A1 * | 3/2009 | TeKolste | G01J 3/18 356/454 |
| 2009/0225277 A1 | 9/2009 | Gil | |
| 2009/0268045 A1 | 10/2009 | Sur et al. | |
| 2010/0069758 A1 | 3/2010 | Barnes et al. | |
| 2010/0140461 A1 | 6/2010 | Sprigle et al. | |
| 2010/0328659 A1 | 12/2010 | Bodkin | |
| 2011/0069189 A1 | 3/2011 | Venkataraman et al. | |
| 2011/0141569 A1 | 6/2011 | Wehner | |
| 2013/0130428 A1 * | 5/2013 | TeKolste | H01L 27/14685 438/70 |
| 2015/0177429 A1 | 6/2015 | Darty | |
| 2017/0371079 A1 | 12/2017 | Darty | |

FOREIGN PATENT DOCUMENTS

| | | |
|---|---|---|
| JP | 2003-230157 A | 8/2003 |
| JP | 2004-228662 A | 8/2004 |
| JP | 2005-511205 A | 4/2005 |
| JP | 2007-020880 A | 2/2007 |
| JP | 2007-293336 A | 11/2007 |
| JP | 2008-525158 T | 7/2008 |
| JP | 2011-143154 | 7/2011 |
| WO | WO 2007/008826 | 1/2007 |
| WO | WO 2011/064403 | 6/2011 |

OTHER PUBLICATIONS

Larson, A.A., et al., "Quantification of Tryptamine in Brain Using High-Performance Liquid Chromatography", J. of Chromatography, v. 375, p. 37-47 (1986).

Wandell, B., et al., "Multiple Capture Single mage Architecture with a CMOS Sensor", In the International Symposium on Multispectral Imaging and Color Reproduction for Digital Archives (1999).

* cited by examiner

SINGLE-SENSOR HYPERSPECTRAL IMAGING DEVICE

CROSS-REFERENCE TO RELATED APPLICATION

This application is a continuation of U.S. patent application Ser. No. 16/003,036, filed Jun. 7, 2018, which is a continuation of U.S. patent application Ser. No. 15/681,265, filed Aug. 18, 2017, which is a continuation of U.S. patent application Ser. No. 13/844,737, filed Mar. 15, 2013, which claims priority to U.S. Provisional Patent Application Ser. No. 61/716,401, filed Oct. 19, 2012, U.S. Provisional Patent Application Ser. No. 61/715,273, filed Oct. 17, 2012, and U.S. Provisional Patent Application Ser. No. 61/655,800, filed Jun. 5, 2012, the disclosures of which are hereby incorporated by reference in their entireties for all purposes.

TECHNICAL FIELD

The present disclosure generally relates to hyperspectral spectroscopy, and in particular, to systems, methods and devices enabling a single-sensor hyperspectral imaging device.

BACKGROUND

Hyperspectral (also known as "multispectral") spectroscopy is an imaging technique that integrates multiple images of an object resolved at different spectral bands (i.e., ranges of wavelengths) into a single data structure, referred to as a three-dimensional hyperspectral data cube. Data provided by hyperspectral spectroscopy is often used to identify a number of individual components of a complex composition through the recognition of spectral signatures of the individual components of a particular hyperspectral data cube.

Hyperspectral spectroscopy has been used in a variety of applications, ranging from geological and agricultural surveying to military surveillance and industrial evaluation. Hyperspectral spectroscopy has also been used in medical applications to facilitate complex diagnosis and predict treatment outcomes. For example, medical hyperspectral imaging has been used to accurately predict viability and survival of tissue deprived of adequate perfusion, and to differentiate diseased (e.g. tumor) and ischemic tissue from normal tissue.

Hyperspectral/multispectral spectroscopy has also been used in medical applications to assist with complex diagnosis and predict treatment outcomes. For example, medical hyperspectral/multispectral imaging has been used to accurately predict viability and survival of tissue deprived of adequate perfusion, and to differentiate diseased (e.g. tumor) and ischemic tissue from normal tissue. (See, Colarusso P. et al., Appl Spectrosc 1998; 52:106A-120A; Greenman R. I. et al., Lancet 2005;366:1711-1718; and Zuzak K. J. et al., Circulation 2001; 104(24):2905-10; the contents of which are hereby incorporated herein by reference in their entireties for all purposes.)

However, despite the great potential clinical value of hyperspectral imaging, several drawbacks have limited the use of hyperspectral imaging in the clinic setting. In particular, current medical hyperspectral instruments are costly because of the complex optics and computational requirements currently used to resolve images at a plurality of spectral bands to generate a suitable hyperspectral data cube. Hyperspectral imaging instruments can also suffer from poor temporal and spatial resolution, as well as low optical throughput, due to the complex optics and taxing computational requirements needed for assembling, processing, and analyzing data into a hyperspectral data cube suitable for medical use.

Thus, there is an unmet need in the field for less expensive and more rapid means of hyperspectral/multispectral imaging and data analysis. The present disclosure meets these and other needs by providing methods and systems for co-axial hyperspectral/multispectral imaging.

SUMMARY

Various implementations of systems, methods and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various implementations are used to enable a hyperspectral imaging device capable of producing a three-dimensional hyperspectral data cube using a single photo-sensor chip (e.g. CDD, CMOS, etc) suitable for use in a number for applications, and in particular, for medical use.

BRIEF DESCRIPTION OF THE DRAWINGS

So that the present disclosure can be understood in greater detail, a more particular description may be had by reference to the features of various implementations, some of which are illustrated in the appended drawings. The appended drawings, however, merely illustrate the more pertinent features of the present disclosure and are therefore not to be considered limiting, for the description may admit to other effective features and arrangements.

Figure 1:
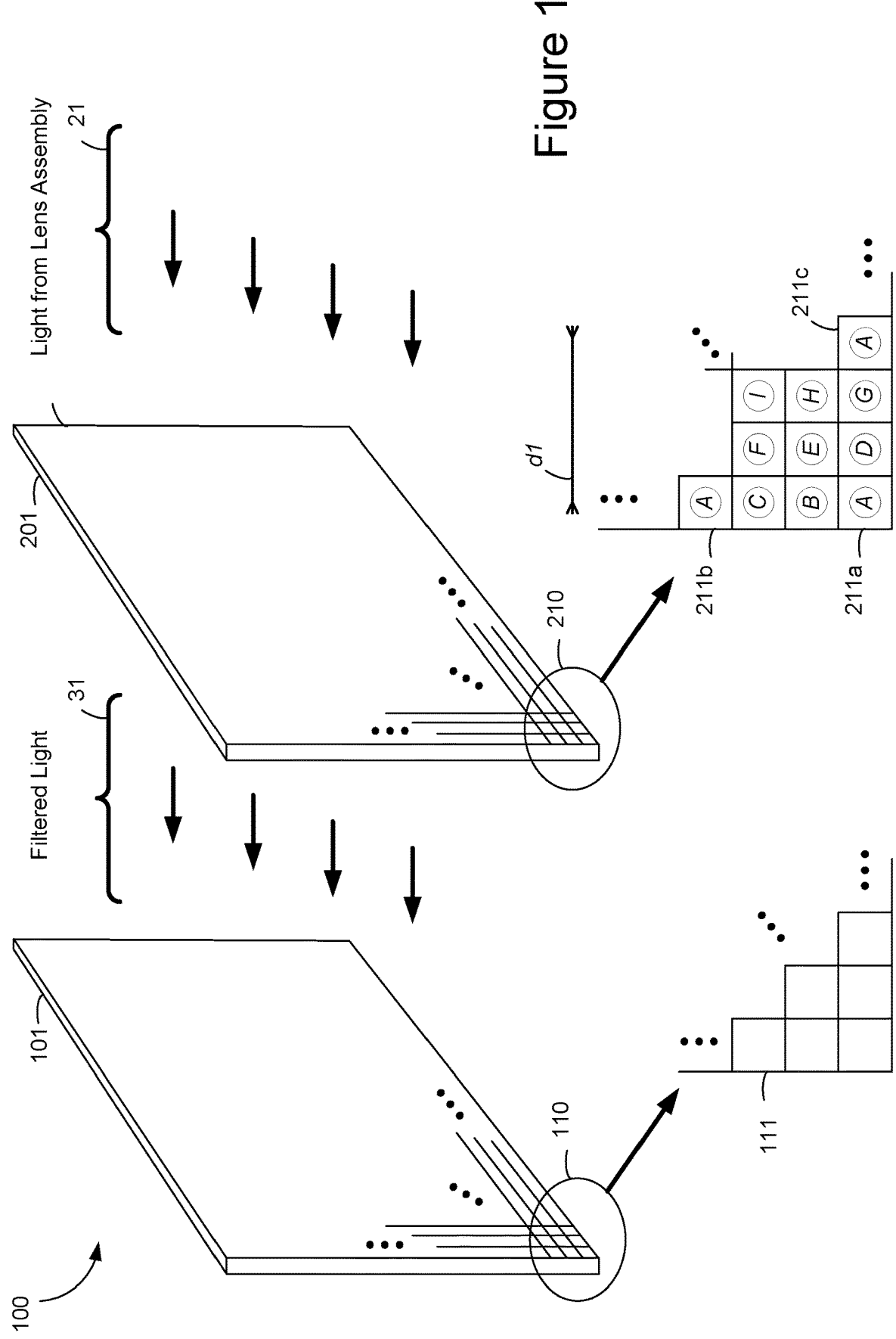
FIG. 1 is an illustration of a spectral filter array 201 having nine filter elements (A-I), each filter element 211 corresponding to a pixel 111 on detector 101.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

The present invention hereby incorporates by reference U.S. Patent Provisional Application Nos. 61/655,800, filed Jun. 5, 2012 and 61/715,273, filed Oct. 17, 2012. Numerous details are described herein in order to provide a thorough understanding of the example implementations illustrated in the accompanying drawings. However, the invention may be practiced without many of the specific details. And, well-known methods, components, and circuits have not been described in exhaustive detail so as not to unnecessarily obscure more pertinent aspects of the implementations described herein.

FIG. 1 is an exploded schematic view of an implementation of an image sensor assembly 100 for a single-sensor hyperspectral imaging device. The image sensor assembly 100 includes a photo-sensory array 101 in combination with a filter array 201. While some example features are illustrated in FIG. 1, those skilled in the art will appreciate from the present disclosure that various other features have not been illustrated for the sake of brevity and so as not to obscure more pertinent aspects of the example implementations disclosed herein. For example, the various electrical connections and access control circuitry to receive the outputs of the photo-sensor array 101 have not been illustrated. Nevertheless, those skilled in the art will appreciate that at least one of various configurations of electrical connections and access control circuitry to receive the outputs of the photo-sensor array 101 would be included in an operable single-sensor hyperspectral imaging device. Moreover, an interface module and a controller—which are together configured to select, assemble, process, and analyze the outputs of the photo-sensor array 101 into a hyperspectral data cube—are described below with reference to FIG. 2.

With further reference to FIG. 1, in some implementations, the photo-sensory array 101 includes a plurality of photo-sensors. For example, the detailed view 110 schematically shows, as a non-limiting example only, a number of photo-sensors 111 included in the photo-sensor array 101. Each photo-sensor 111 generates a respective electrical output by converting light incident on the photo-sensor.

In some implementations, the photo-sensor array 101 includes a CCD (charge coupled device) semiconductor sensor array. A CCD sensor is typically an analog device. When light strikes the CCD sensor array, the light is converted to and stored as an electrical charge in each photo-sensor. The charges are converted to voltage one photo-sensor (often, but not exclusively, synonymous with a pixel) at a time as they are read from the CCD sensor array.

In some implementations, the photo-sensor array 101 includes a CMOS (complementary metal oxide) semiconductor sensor array. A CMOS photo-sensor is an active photo-sensor that includes a photodetector and an active amplifier. In other words, each photo-sensor in a CMOS sensor array includes a respective photodetector and a corresponding active amplifier.

In some implementations, the photo-sensor array 101 includes a hybrid CCD/CMOS sensor array. In some implementations, a hybrid CCD/CMOS sensor array includes CMOS readout integrated circuits (ROICs) that are bump bonded to a CCD imaging substrate. In some implementations, a hybrid CCD/CMOS sensor array is produced by utilizing the fine dimensions available in modern CMOS technology to implement a CCD like structure in CMOS technology. This can be achieved by separating individual poly-silicon gates by a very small gap.

The light incident on a particular photo-sensor 111 is filtered by a respective filter in the filter array 201. In some implementations, the filter array 201 is configured to include a plurality of filter elements. Each filter element is arranged to filter light received by a respective one or more of the plurality of photo-sensors in the photo-sensor array 101. Each filter element is also one of a plurality of filter-types, and each filter-type is characterized by a spectral pass-band different from the other filter-types. As such, the electrical output of a particular photo-sensor is associated with a particular spectral pass-band associated with the respective filter associated the particular photo-sensor 111.

For example, the detailed view 210 schematically shows, as a non-limiting example only, a number of filter-types A, B, C, D, E, F, G, H, I included in the filter array 201. Each filter-type A, B, C, D, E, F, G, H, I has a spectral pass-band different from the others, The filter-types A, B, C, D, E, F, G, H, I are arranged in a 3×3 grid that is repeated across the filter array 201. For example, as illustrated in FIG. 1, three filters 211a, 211b, 211c of filter-type A are illustrated to show that instances of filter-type A are repeated in a uniform distribution across the filter array 201 such that the center-to-center distance d1 between two filters of the same type is less than 250 microns in some implementations. In some implementations, the center-to-center distance d1 between two filters of the same type is less than 100 microns.

Moreover, while nine filter-types are illustrated for example in FIG. 1, those skilled in the art will appreciate from the present disclosure that any number of filter types can be used in various implementations. For example, in some implementations 3, 5, 16 or 25 filter-types can be used in various implementations. Additionally and/or alternatively, while a uniform distribution of filter-types has been illustrated and described, those skilled in the art will appreciate from the present disclosure that, in various implementations, one or more filter-types may be distributed across a filter array in a non-uniform distribution. Additionally and/or alternatively, those skilled in the art will also appreciate that "white-light" or transparent filter elements may be included as one of the filter-types in a filter array.

Figure 2:
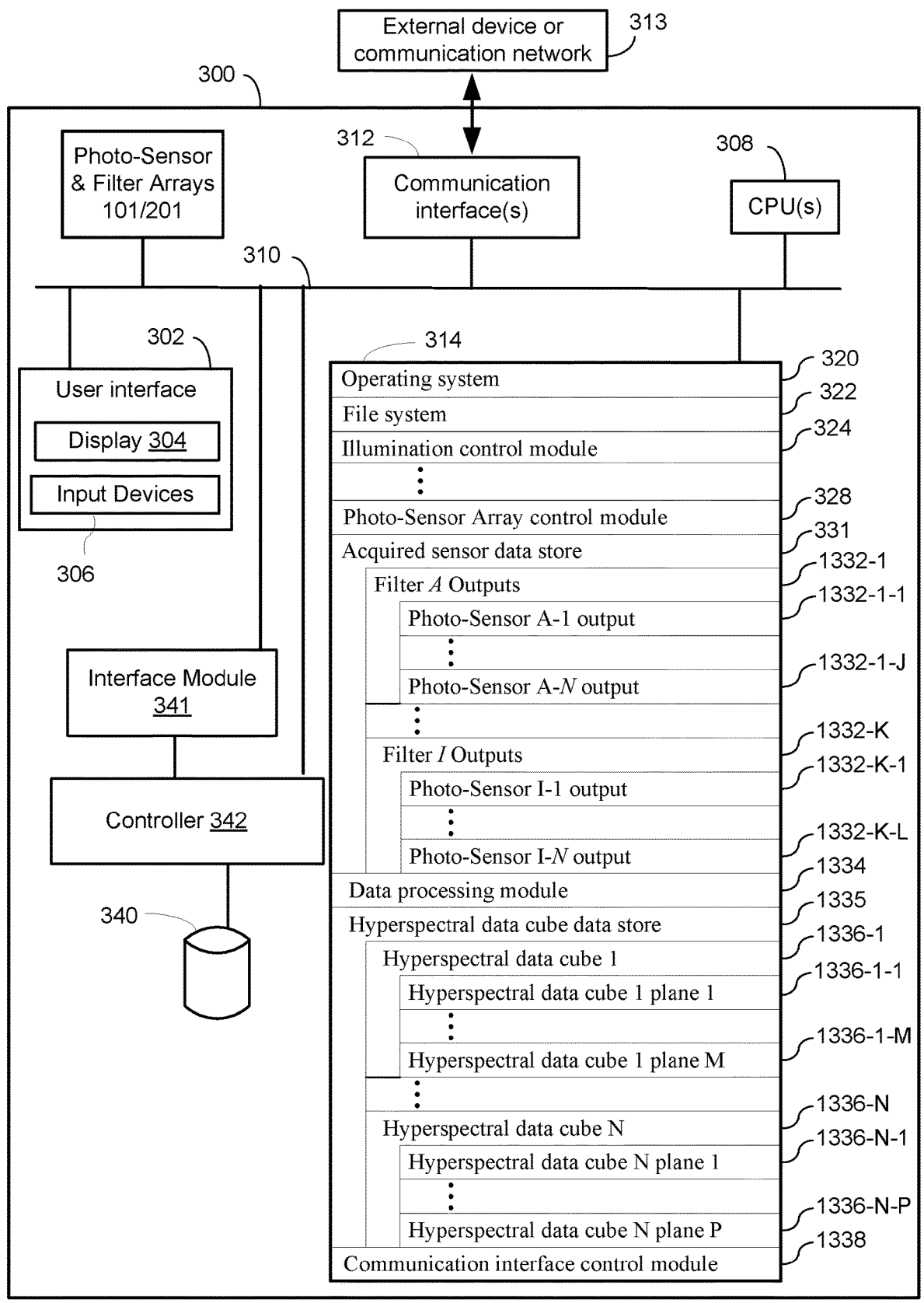
FIG. 2 schematically illustrates a processing subsystem for a hyperspectral/multispectral system, according to some embodiments.

FIG. 2 is a block diagram of an implementation of a single-sensor hyperspectral imaging device 300 (hereinafter referred to as "imaging device 300" for brevity). While some example features are illustrated in FIG. 2, those skilled in the art will appreciate from the present disclosure that various other features have not been illustrated for the sake of brevity and so as not to obscure more pertinent aspects of the example implementations disclosed herein. To that end, the imaging device 300 includes one or more central processing units (CPU) 308, an optional main non-volatile storage unit 340, a controller 342, a system memory 314 for storing system control programs, data, and application programs, including programs and data optionally loaded from the non-volatile storage unit 340. In some implementations the non-volatile storage unit 340 includes a memory card for storing software and data. The storage unit 340 is optionally controlled by the controller 342.

In some implementations, the imaging device 300 optionally includes a user interface 302 including one or more input devices 306 (e.g., a touch screen, buttons, or switches) and/or an optional display 304. Additionally and/or alternatively, in some implementations, the imaging device 300 may be controlled by an external device such as a handheld device, a smartphone (or the like), a tablet computer, a laptop computer, a desktop computer, and/or a server system. To that end, the imaging device 300 includes one or more communication interfaces 312 for connecting to any wired or wireless external device or communication network (e.g. a wide area network such as the Internet) 313. The imaging device 300 includes an internal bus 310 for interconnecting the aforementioned elements. The communication bus 310 may include circuitry (sometimes called a chipset) that interconnects and controls communications between the aforementioned components.

In some implementations, the imaging device 300 communicates with a communication network 313, thereby enabling the imaging device 300 to transmit and/or receive data between mobile communication devices over the communication network, particularly one involving a wireless link, such as cellular, WiFi, ZigBee, BlueTooth, IEEE 802.11b, 802.11a, 802.11g, or 802.11n, etc. The communication network can be any suitable communication network configured to support data transmissions. Suitable communication networks include, but are not limited to, cellular networks, wide area networks (WANs), local area networks (LANs), the Internet, IEEE 802.11b, 802.11a, 802.11g, or 802.11n wireless networks, landline, cable line, fiber-optic line, etc. The imaging system, depending on an embodiment or desired functionality, can work completely offline by virtue of its own computing power, on a network by sending raw or partially processed data, or both simultaneously.

The system memory 314 includes high-speed random access memory, such as DRAM, SRAM, DDR RAM, or other random access solid state memory devices; and typically includes non-volatile memory flash memory devices, or other non-transitory solid state storage devices. The system memory 314 optionally includes one or more storage devices remotely located from the CPU(s) 308. The system memory 314, or alternately the non-transitory memory device(s) within system memory 314, comprises a non-transitory computer readable storage medium.

In some implementations, operation of the imaging device 300 is controlled primarily by an operating system 320, which is executed by the CPU 308. The operating system 320 can be stored in the system memory 314 and/or storage unit 340. In some embodiments, the image device 300 is not controlled by an operating system, but rather by some other suitable combination of hardware, firmware and software.

In some implementations, the system memory 314 includes one or more of a file system 322 for controlling access to the various files and data structures described herein, an illumination software control module 324 for controlling a light source associated and/or integrated with the imaging device 300, a photo-sensor array software control module 328, a sensor data store 331 for storing sensor data 1332 acquired by the photo-sensor array 101, a data processing software module 1334 for manipulating the acquired sensor data, a hyperspectral data cube data store 1335 for storing hyperspectral data cube data 1336 assembled from the acquired sensor, and a communication interface software control module 1338 for controlling the communication interface 312 that connects to an external device (e.g., a handheld device, laptop computer, or desktop computer) and/or communication network (e.g. a wide area network such as the Internet).

In some implementations, the acquired sensor data 1332 is arranged and stored by the filter-type associated with each photo-sensor 111 in the photo-sensor array 101. For example, as illustrated in FIG. 2, the photo-sensor output data 1332-1 from the photo-sensors associated with filter-type A are selectable from the photo-sensor output data, such as photo-sensor output data 1332-K associated with filter-type I.

The acquired sensor data 1332 and hyperspectral data cube data 1336 can be stored in a storage module in the system memory 314, and do not need to be concurrently present, depending on which stages of the analysis the imaging device 300 has performed at a given time. In some implementations, prior to imaging a subject and after communicating the acquired sensor data or processed data files thereof, the imaging device 300 contains neither acquired sensor data 1332 nor the hyperspectral data cube data 1336. In some implementations, after imaging a subject and after communicating the acquired sensor data or processed data files thereof, the imaging device 300 retains the acquired sensor data 1332 and/or hyperspectral data cube data 1336 for a period of time (e.g., until storage space is needed, for a predetermined amount of time, etc.).

In some implementations, the programs or software modules identified above correspond to sets of instructions for performing a function described above. The sets of instructions can be executed by one or more processors, e.g., a CPU(s) 308. The above identified software modules or programs (e.g., sets of instructions) need not be implemented as separate software programs, procedures, or modules, and thus various subsets of these programs or modules may be combined or otherwise re-arranged in various embodiments. In some embodiments, the system memory 314 stores a subset of the modules and data structures identified above. Furthermore, the system memory 314 may store additional modules and data structures not described above.

The system memory 314 optionally also includes one or more of the following software modules, which are not illustrated in FIG. 1: a spectral library which includes profiles for a plurality of medical conditions, a spectral analyzer software module to compare measured hyperspectral data to a spectral library, control modules for additional sensors; information acquired by one or more additional sensors, an image constructor software module for generating a hyperspectral image, a hyperspectral image assembled based on a hyperspectral data cube and optionally fused with information acquired by an additional sensor, a fusion software control module for integrating data acquired by an additional sensor into a hyperspectral data cube, and a display software control module for controlling a built-in display.

While examining a subject and/or viewing hyperspectral images of the subject, a physician can optionally provide input to the image device 300 that modifies one or more parameters upon which a hyperspectral image and/or diagnostic output is based. In some implementations, this input is provided using input device 306. Among other things, the image device can be controlled to modify the spectral portion selected by a spectral analyzer (e.g., to modify a threshold of analytical sensitivity) or to modify the appearance of the image generated by an image assembler (e.g., to switch from an intensity map to a topological rendering).

In some implementations, the imaging device 300 can be instructed to communicate instructions to an imaging subsystem to modify the sensing properties of one of the photo-sensor array 101 and the filter array 201 (e.g., an exposure setting, a frame rate, an integration rate, or a wavelength to be detected). Other parameters can also be modified. For example, the imaging device 300 can be instructed to obtain a wide-view image of the subject for screening purposes, or to obtain a close-in image of a particular region of interest.

In some implementations, the imaging device 300 does not include a controller 342 or storage unit 340. In some such implementations, the memory 314 and CPU 308 are one or more application-specific integrated circuit chips (ASICs) and/or programmable logic devices (e.g. an FGPA—Field Programmable Gate Array). For example, in some implementations, an ASIC and/or programmed FPGA includes the instructions of the illumination control module 324, photo-sensor array control module 328, the data processing module 334 and/or communication interface control module 338. In some implementations, the ASIC and/or FPGA further includes storage space for the acquired sensor data store 331 and the sensor data 1332 stored therein and/or the hyperspectral data cube data store 1335 and the hyperspectral/multispectral data cubes 1336 stored therein.

In some implementations, the system memory 314 includes a spectral library and spectral analyzer for comparing hyperspectral data generated by the image device 300 to known spectral patterns associated with various medical conditions. In some implementations, analysis of the acquired hyperspectral data is performed on an external device such as a handheld device, tablet computer, laptop computer, desktop computer, an external server, for example in a cloud computing environment.

In some implementations, a spectral library includes profiles for a plurality of medical conditions, each of which contain a set of spectral characteristics unique to the medical condition. A spectral analyzer uses the spectral characteristics to determine the probability that a region of the subject corresponding to a measured hyperspectral data cube is afflicted with the medical condition. In some implementations, each profile includes additional information about the condition, e.g., information about whether the condition is malignant or benign, options for treatment, etc. In some implementations, each profile includes biological information, e.g., information that is used to modify the detection conditions for subjects of different skin types. In some implementations, the spectral library is stored in a single database. In other implementations, such data is instead stored in a plurality of databases that may or may not all be hosted by the same computer, e.g., on two or more computers addressable by wide area network. In some implementations, the spectral library is electronically stored in the storage unit 340 and recalled using the controller 342 when needed during analysis of hyperspectral data cube data.

In some implementations, the spectral analyzer analyzes a particular spectra derived from hyperspectral data cube data, the spectra having pre-defined spectral ranges (e.g., spectral ranges specific for a particular medical condition), by comparing the spectral characteristics of a pre-determined medical condition to the subject's spectra within the defined spectral ranges. Performing such a comparison only within defined spectral ranges can both improve the accuracy of the characterization and reduce the computational power needed to perform such a characterization.

In some implementations, the display 304 which receives an image (e.g., a color image, mono-wavelength image, or hyperspectral/multispectral image) from a display control module, and displays the image. Optionally, the display subsystem also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

In some implementations, a housing display is built into the housing of the imaging device 300. In an example of such an implementation, a video display in electronic communication with the processor 308 is included. In some implementations, the housing display is a touchscreen display that is used to manipulate the displayed image and/or control the image device 300.

In some implementations, the communication interface 312 comprises a docking station for a mobile device having a mobile device display. A mobile device, such as a smart phone, a personal digital assistant (PDA), an enterprise digital assistant, a tablet computer, an IPOD, a digital camera, or a portable music player, can be connected to the docking station, effectively mounting the mobile device display onto the imaging device 300. Optionally, the mobile device is used to manipulate the displayed image and/or control the image device 300.

In some implementations, the imaging device 300 is configured to be in wired or wireless communication with an external display, for example, on a handheld device, tablet computer, laptop computer, desktop computer, television, IPOD, or projector unit, on which the image is displayed. Optionally, a user interface on the external device is used to manipulate the displayed image and/or control the imaging device 300.

In some implementations, an image can be displayed in real time on the display. The real-time image can be used, for example, to focus an image of the subject, to select an appropriate region of interest, and to zoom the image of the subject in or out. In one embodiment, the real-time image of the subject is a color image captured by an optical detector that is not covered by a detector filter. In some implementations, the imager subsystem comprises an optical detector dedicated to capturing true color images of a subject. In some implementations, the real-time image of the subject is a monowavelength, or narrow-band (e.g., 10-50 nm), image captured by an optical detector covered by a detector filter. In some embodiments, the narrow-band filter has a full-width half maximum spectral bandwidth of no more than 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, or 1 nm. In these embodiments, any optical detector covered by a detector filter in the imager subsystem may be used for: (i) resolving digital images of the subject for integration into a hyperspectral data cube; and (ii) resolving narrow-band images for focusing, or otherwise manipulating the optical properties of the imaging device 300.

In some implementations, a hyperspectral image constructed from data collected by the photo-sensor array 101 is displayed on an internal housing display, mounted housing display, or external display. Assembled hyperspectral data (e.g., present in a hyperspectral/multispectral data cube) is used to create a two-dimensional representation of the imaged object or subject, based on one or more parameters. An image constructor module, stored in the imaging system memory or in an external device, constructs an image based on, for example, an analyzed spectra. Specifically, the image constructor creates a representation of information within the spectra. In one example, the image constructor constructs a two-dimensional intensity map in which the spatially-varying intensity of one or more particular wavelengths (or wavelength ranges) within the spectra is represented by a corresponding spatially varying intensity of a visible marker.

In some implementations, the image constructor fuses a hyperspectral image with information obtained from one or more additional sensors. Non-limiting examples of suitable image fusion methods include: band overlay, high-pass filtering method, intensity hue-saturation, principle component analysis, and discrete wavelet transform.

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A hyperspectral imaging device comprising:
   a photo-sensor array including a plurality of photo-sensors, each photo-sensor in the plurality of photo-sensors providing a respective output;
   a spectral filter array having a plurality of filter elements, wherein:
     each filter element in the plurality of filter elements is arranged to filter light received by one respective photo-sensor in the plurality of photo-sensors,
     each photo-sensor in the plurality of photo-sensors is a single pixel,
     each filter element is one of a plurality of filter-types,
     each filter-type is characterized by a spectral pass-band different from the other filter-types, and
     each filter element is a narrow pass filter having a full-width at half-maximum spectral bandwidth of no more than 25 nm;
   one or more processors; and
   memory including instructions, the instructions, when executed by the one or more processors, cause the hyperspectral imaging device to perform operations comprising:
     capturing single frame image data of a tissue of a subject by controlling the exposure of the photo-sensor array to light,
     selecting a plurality of subsets of photo-sensor outputs from the single frame image data of the tissue, wherein each subset of photo-sensor outputs is associated with a single respective filter-type; and
     forming a hyperspectral data cube from the plurality of subsets of photo-sensor outputs by generating a plurality of images, wherein each respective image in the plurality of images is produced from a single corresponding subset of photo-sensor outputs in the plurality of photo-sensor outputs so that each respective image is associated with a corresponding filter-type in the plurality of filter-types.

2. The hyperspectral image device of claim 1, wherein each of the plurality of images is generated by applying an interpolation process to a respective sub-set of photo-sensor outputs for the one respective filter-type.

3. The hyperspectral imaging device of claim 1, wherein a center-to-center distance between two filter elements of the same type is less than 250 microns.

4. The hyperspectral imaging device of claim 1, wherein a center-to-center distance between two filter elements of the same type is less than 150 microns.

5. The hyperspectral imaging device of claim 1, wherein the filter elements of at least one particular filter-type are spatially distributed across throughout the spectral filter array.

6. The hyperspectral imaging device of claim 5, wherein the spatial distribution of the filter elements of the at least one particular filter-type is characterized by a substantially uniform distribution of the filter elements throughout the spectral filter array.

7. The hyperspectral imaging device of claim 5, wherein the spatial distribution of the filter elements of the at least one particular filter-type is characterized by a non-uniform distribution of the filter elements throughout the spectral filter array.

8. The hyperspectral imaging device of claim 1, wherein a spatial distribution of the filter elements is characterized by a repeating pattern of one or more filter- types.

9. The hyperspectral imaging device of claim 1, wherein the plurality of filter-types includes at least three filter-types.

10. The hyperspectral imaging device of claim 1, wherein the instructions, when executed by the one or more processors, further cause the hyperspectral imaging device to:
    receive the output of the photo-sensor array at one or more registers;
    identify which registers correspond to filter elements of a particular filter-type from a look-up table; and
    select one or more sub-sets of photo-sensor outputs from the one or more registers based on the identification of the registers that correspond to filter elements of the particular filter-type.

11. The hyperspectral imaging device of claim 10, wherein the instructions, when executed by the one or more processors, further cause the hyperspectral imaging device to bundle photo-sensor outputs from the particular filter-type into data packets, wherein the data packets include at least the corresponding register values.

12. The hyperspectral imaging device of claim 11, further comprising a transceiver to transmit the data packets to a server, and receive an image for each filter-type from the server based on the transmitted data packets.

13. The hyperspectral imaging device of claim 1, comprising a hand-held medical imaging device.

14. The hyperspectral imaging device of claim 1, wherein the instructions, when executed by the one or more processors, further cause the hyperspectral imaging device to process the plurality of photo-sensor outputs.

15. The hyperspectral imaging device of claim 1, wherein the instructions, when executed by the one or more processors, further cause the hyperspectral imaging device to determine, using the hyperspectral data cube generated from the single frame image data of the tissue of the subject, a probability that a region of the interest of the subject has a particular medical condition, a category of condition, a probable age of a condition, a boundary of a condition, or information about treatment of a condition.

16. The hyperspectral imaging device of claim 1, further comprises a display, wherein the instructions, when executed by the one or more processors, further cause the hyperspectral imaging device to display a hyperspectral image of the tissue formed by the hyperspectral data cube on the display.

17. The hyperspectral imaging device of claim 16, wherein the instructions, when executed by the one or more processors, further cause the hyperspectral imaging device to display a probability that the tissue has a particular medical condition, a category of condition, a probable age of a condition, a boundary of a condition, or information about treatment of a condition.

18. The hyperspectral imaging device of claim 16, wherein the display is a touchscreen display that is used to manipulate a displayed image or to control the hyperspectral imaging device.

19. The hyperspectral imaging device of claim 1, further comprising a communication interface for communicating the plurality of images or the hyperspectral data cube to a remote device across a communication network.

* * * * *